United States Patent
Steinhardt et al.

(10) Patent No.: US 9,259,311 B2
(45) Date of Patent: Feb. 16, 2016

(54) OSSICLE PROSTHESIS COMPRISING A BUILT-UP ATTACHING ELEMENT

(71) Applicant: HEINZ KURZ GMBH MEDIZINTECHNIK, Dusslingen (DE)

(72) Inventors: Uwe Steinhardt, Hirrlingen (DE); Seilesh Babu, Novi, MI (US); Heinz Kurz, Dusslingen (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 0 days.

(21) Appl. No.: 14/246,443

(22) Filed: Apr. 7, 2014

(65) Prior Publication Data

US 2014/0303728 A1    Oct. 9, 2014

(30) Foreign Application Priority Data

Apr. 8, 2013    (DE) .................... 10 2013 103 484

(51) Int. Cl.
*A61F 2/18*    (2006.01)

(52) U.S. Cl.
CPC ............. *A61F 2/18* (2013.01); *A61F 2002/183* (2013.01)

(58) Field of Classification Search
CPC .............................................. A61F 2002/183
See application file for complete search history.

(56) References Cited

U.S. PATENT DOCUMENTS

| | | | |
|---|---|---|---|
| 5,514,177 A | 5/1996 | Kurz et al. | |
| 6,537,199 B1 | 3/2003 | Mueller | |
| 6,554,861 B2 | 4/2003 | Knox et al. | |
| 6,579,317 B2 | 6/2003 | Kurz | |
| 7,806,931 B2 * | 10/2010 | Huettenbrink et al. | 623/10 |
| 8,100,966 B2 | 1/2012 | Steinhardt et al. | |
| 8,142,500 B2 | 3/2012 | Steinhardt et al. | |
| 8,518,112 B2 | 8/2013 | Lenarz et al. | |
| 2004/0162614 A1 | 8/2004 | Steinhardt et al. | |
| 2008/0208338 A1 | 8/2008 | Steinhardt et al. | |
| 2009/0164010 A1 * | 6/2009 | Steinhardt et al. | 623/10 |
| 2012/0078368 A1 * | 3/2012 | Lenarz | A61F 2/18 623/10 |

FOREIGN PATENT DOCUMENTS

| | | |
|---|---|---|
| DE | 10 2007 008 851 | 6/2008 |
| DE | 10 2008 015 117 | 6/2009 |
| DE | 10 2009 016 468 | 12/2009 |

(Continued)

*Primary Examiner* — Yashita Sharma
*Assistant Examiner* — Wade P Schutte
(74) *Attorney, Agent, or Firm* — Michael J. Striker

(57) ABSTRACT

An ossicular prosthesis formed as a sound-conducting, elongated prosthesis body has a first coupling element designed as a tympanic membrane top plate or a clip or a connecting piece to an actuator end piece of an active hearing implant and a second coupling element provided with an access opening into a receiving space designed as a bell or a clip for a mechanical connection of the prosthesis to the head of the stapes. The second coupling element has a backing section on an inner surface of the receiving space as an axial extension of the prosthesis body. The backing section protrudes from the prosthesis body into the receiving space. In an implanted state, the backing section bears against a head of the stapes and prevents a formation of a hollow space between the stapes and an inner surface of the receiving space in an axial extension of the elongated prosthesis body. As a result, additional degrees of freedom are obtained for individualized adaptation to anatomical circumstances of a specific patient in terms of shape, size and position of the patient's stapes bone.

15 Claims, 16 Drawing Sheets

(56) References Cited

FOREIGN PATENT DOCUMENTS

| DE | 10 2010 046 457 | 7/2011 |
| EP | 1 181 907 | 2/2002 |
| EP | 1 438 931 | 7/2004 |
| WO | 98/16175 | 4/1998 |
| WO | 02/069850 | 9/2002 |

* cited by examiner

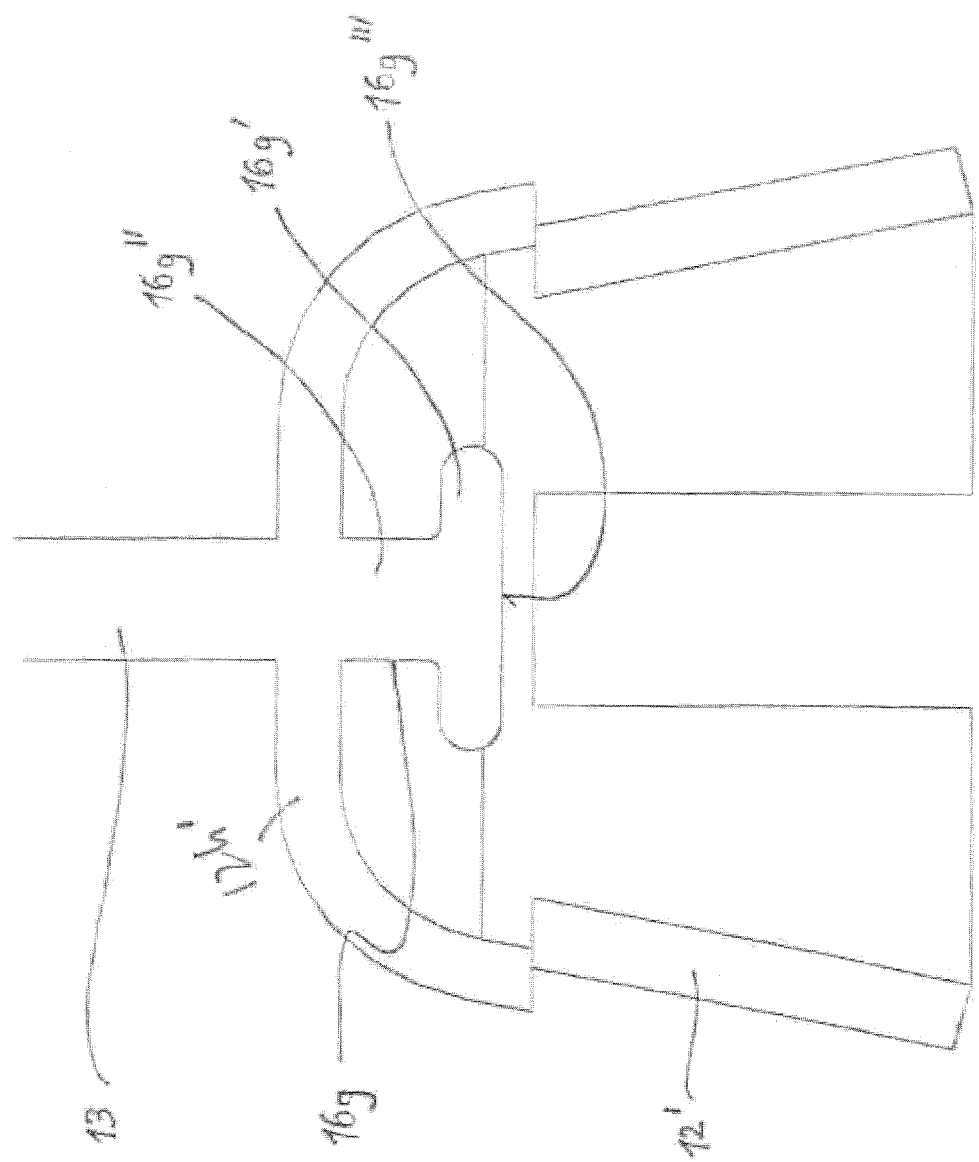

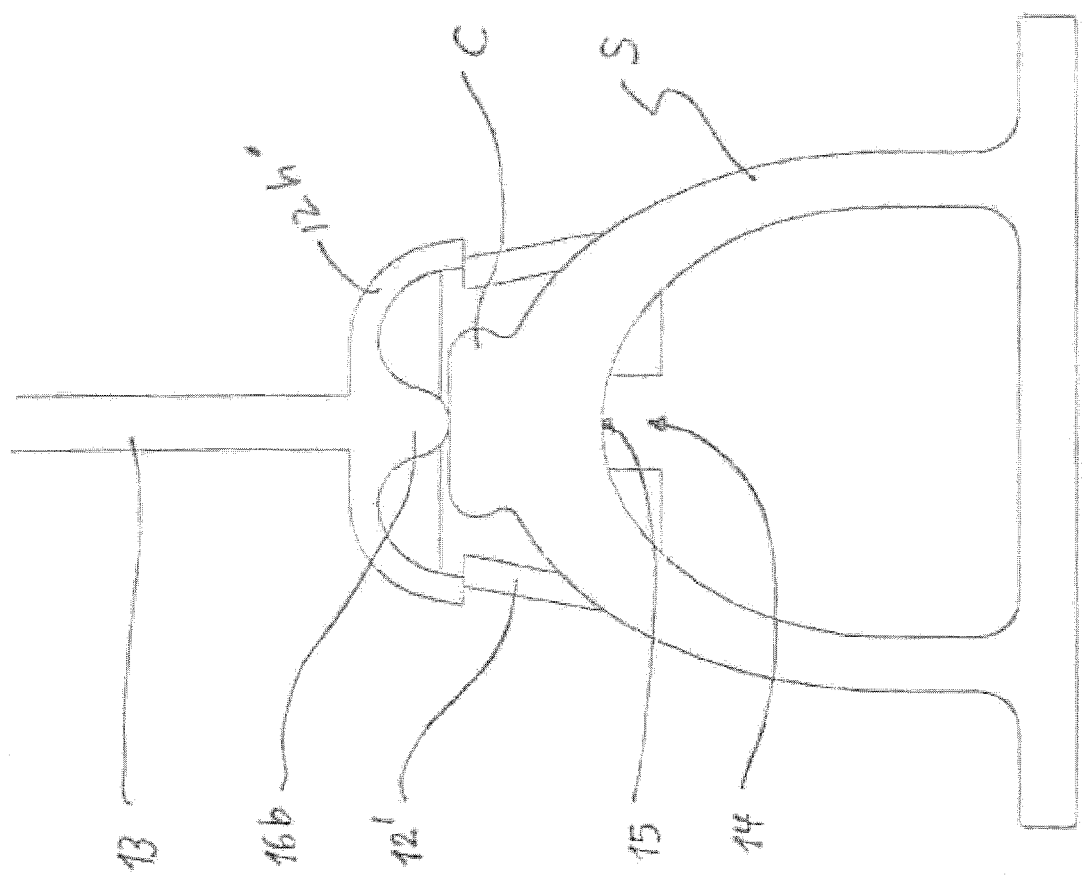

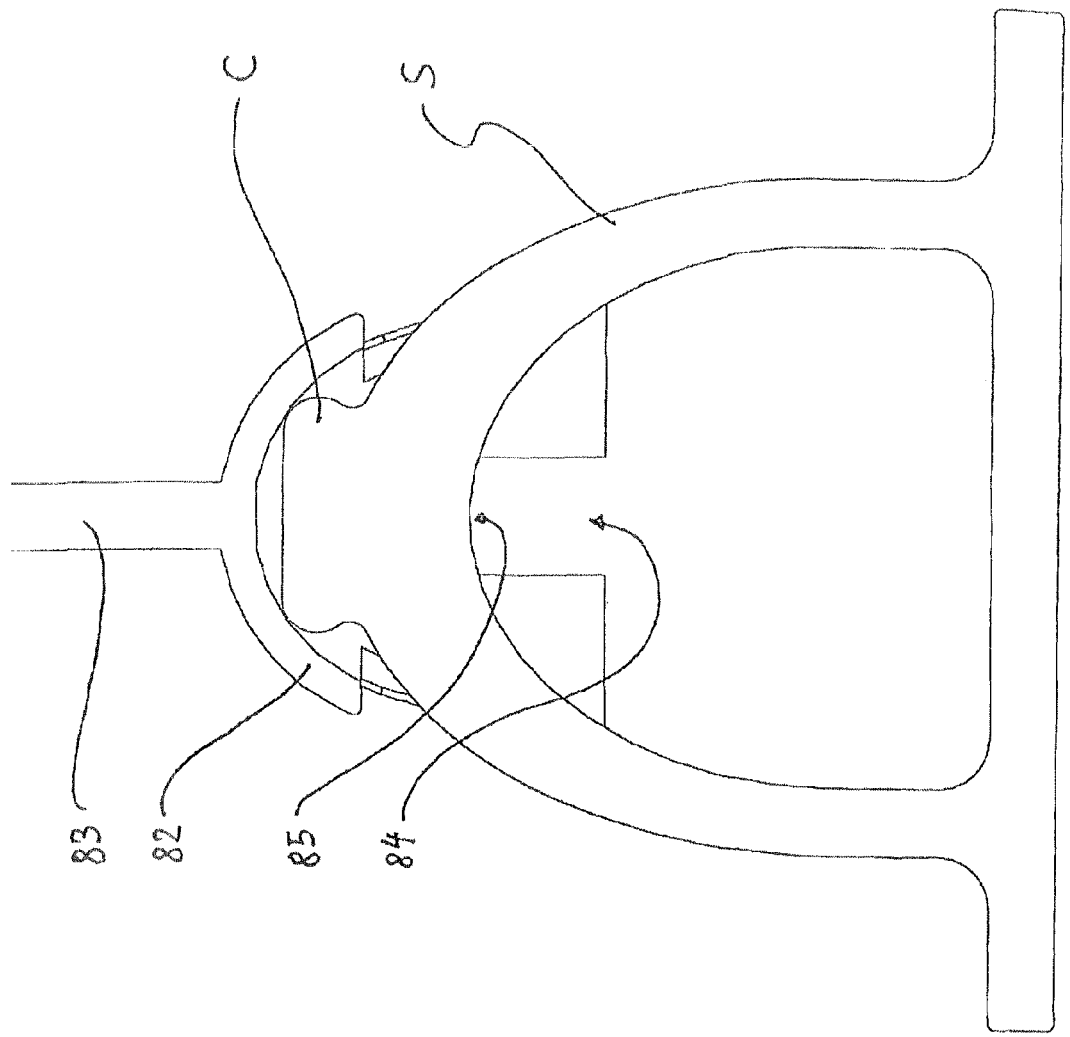

OSSICLE PROSTHESIS COMPRISING A BUILT-UP ATTACHING ELEMENT

CROSS-REFERENCE TO A RELATED APPLICATION

The invention described and claimed hereinbelow is also described in German Priority Document DE 10 2013 103 484.5, filed on Apr. 8, 2013. The German Priority Document, the subject matter of which is incorporated herein by reference, provides the basis for a claim of priority of invention under 35 U.S.C. 119(a)-(d).

BACKGROUND OF THE INVENTION

The invention relates to an active or passive ossicular prosthesis, which is designed to replace or bridge at least one element of the human ossicular chain and comprises a sound-conducting, elongated prosthesis body, which on one end has a first coupling element designed as a top plate for placement of the prosthesis against the tympanic membrane, as a clip for the mechanical connection to a component of the ossicular chain, such as the limb of incus or the manubrium of malleus, or as a connecting piece for the sound-conducting connection to an actuator end piece of an active hearing implant. On the other end, the prosthesis body comprises a second coupling element having an access opening in a receiving space designed as a bell or clip for a mechanical connection of the prosthesis to the stapes, such as the head of stapes ("caput").

Passive ossicular prostheses are described in the field of active hearing implants, such as in U.S. Pat. No. 6,537,199 B1 or, for example, in DE 10 2010 046 457 B3.

In conventional passive ossicular prostheses, such arrangements having differently designed first and second fastening elements are used, such as described in U.S. Pat. No. 5,514,177, in WO 98/16175 A1, in EP 1 181 907 B1, in DE 10 2008 015 117 B3 or in DE 10 2009 016 468 B3.

The human middle ear comprising the ossicles thereof has the function of transmitting the sound waves impacting the tympanic membrane via the external auditory meatus to the inner ear, which is filled with fluid. The three ossicles are the hammer (lat. malleus), which is fastened to the tympanic membrane, the stirrup (lat. stapes), which is connected via the footplate (lat. basis stapedis) thereof to the inner ear, and the anvil (lat. incus), which is located between the hammer and the stapes and is hingedly connected thereto.

Chronic middle ear inflammation is a disease of the human petrosal bone (=bone in which the entire ear is seated), in which degenerative processes can occur on the ossicular chain in a pathologically aggressive manner. As a result, the sound signal is not transmitted to the inner ear, or is transmitted incompletely, which results in conductive deafness.

Hearing implants are used to conduct the sound that impacts the auricle, or a corresponding sound signal, to the inner ear in cases in which the ossicles of the human middle ear are missing or damaged, entirely or in part. A distinction is made between passive ossicular prostheses and active hearing implants. Passive ossicular prostheses physically replace parts of the ossicular chain, wherein sound is conducted "passively", i.e., without the aid of powered auxiliary means. Active hearing implants receive powered signals corresponding to the sound signals from an amplifier by use of an actuator implanted in the middle ear. The amplifier is usually electronic and is associated with an externally or an internally mounted hearing aid. Such active hearing implants convert these signals at this point via mechanical motion back to acoustic oscillations and transmit these from a vibrating actuator end piece to the inner ear via a suitable connecting element.

Passive ossicular prostheses are used to improve sound transmission in patients having different pathologies. These passive ossicular prostheses are used to conduct sound from the tympanic membrane to the inner ear in cases in which the ossicles of the human middle ear are missing or damaged, either entirely or partially. The ossicular prosthesis has two ends. Depending on the specific circumstances, one end of the ossicular prosthesis is fastened to the tympanic membrane, e.g., using a top plate, and the other end of the ossicular prosthesis is fastened to the stapes of the human ossicular chain, or it is inserted directly into the inner ear. In the known ossicular prostheses, sound conduction between the tympanic membrane and the inner ear is often limited because these known ossicular prostheses cannot fully replace the natural anatomical formations of the ossicular chain and the mechanisms of the middle ear, which have fine structures.

Three types of ossicular prostheses that are used particularly frequently are stapes prostheses, partial prostheses and total prostheses. Stapes prostheses are fixed to the incus and extend via a plunger into the inner ear. Partial prostheses typically bear via a top plate against the tympanic membrane and establish a connection to the head of the stapes. Total prostheses connect the tympanic membrane to the base of the stapes. The present invention relates exclusively to partial prostheses.

As shown clearly in the three enlarged photographs of more or less pathological human ear stapes bones in FIGS. 9a, 9b and 9c, the anatomical differences are drastic in terms of shape and absolute size. That is, the respective detailed views of FIGS. 9a-c specifically highlight the region of the head of the stapes, which is precisely where the above-described partial prostheses are supposed to be coupled via the second attaching element thereof. A truly optimal coupling at this position would therefore require that the shaping of the particular coupling element on the implant that is used be adapted in an entirely individualized manner for each patient, which cannot be done, of course, at a reasonable expense.

For that matter, a notable detail problem is that, in the case of the common forms of coupling elements that are known and have been used for many years (for example in embodiments such as a stapes bell, or when clips are used), a hollow space practically always forms as an extension of the shank-shaped prosthesis body between the inner side of the attaching element and the upper region of the head of the stapes because the stapes upper region usually has a somewhat flattened shape, while the coupling elements typically used at this point are concavely arched.

SUMMARY OF THE INVENTION

The present invention overcomes the shortcomings of known arts, such as those mentioned above.

To that end, the present invention provides an improvement of an active or passive ossicular prosthesis of the originally described type in a most cost-favorable manner possible and using the simplest technical means in such a way that the above-described advantages of the known partial prostheses for handling in the region of the middle ear and the resultant improvement of sound transmission are retained.

The inventive prosthesis construction, however, after implantation, reliably prevents the formation of a hollow space in the axial extension of the prosthesis body between the inner side of the attaching element and the upper region of the head of the stapes. Moreover, further degrees of freedom are obtained for the individualized adaptation to the anatomical circumstances of the specific patient in terms of shape, size and position of the patients stapes bone.

According to the invention, the second coupling element comprises a backing section on the inner surface of the receiving space, as an axial extension of the elongated prosthesis body. The backing section projects from the prosthesis body into the receiving space. In the implanted state of the ossicular prosthesis, the backing section bears against the stapes, in particular against the head of the stapes, and prevents or minimizes the formation of a hollow space between the stapes and the inner surface of the receiving space in the axial extension of the elongated prosthesis body. The ossicular prosthesis is therefore provided with a seat on the stapes that is slip-resistant and positionally stable for relatively long periods of time, and wherein sound transmission is improved because a hollow space which obstructs sound is no longer formed therebetween.

In an embodiment of the ossicular prosthesis, the second coupling element is designed as a bell having several lateral slots and is fastened via the bell hood at one end of the elongated prosthesis body. The advantage provided by the slots in the bell is that the prosthesis can be slipped over the stapes even if the uppermost part of the stapes would be missing. In a variant of this embodiment, the bell has a roundly arched bell hood.

Alternatively, however, the bell comprises a bell hood that is flattened and/or indented from above, which has the advantage that contact always occurs in the axial extension of the shank making it possible to also clearly specify the length of the prosthesis.

In an embodiment, the second coupling element is designed as a clip comprising a plurality of respectively alternating, lateral blades and slots. This type of coupling element is often used in cases where high stability is required intra-surgically, and therefore the surgeon utilizes a technically simple application.

The backing section is preferably spherical or ellipsoid in shape and is disposed symmetrically relative to the extended axis of the elongated prosthesis body, thereby ensuring that direct contact with the stapes always occurs.

In an embodiment of the ossicular prosthesis, the backing section is conical in shape and is disposed symmetrically relative to the extended axis of the elongated prosthesis body. In this case, the cone tip protrudes from the elongated prosthesis body into the receiving space resulting in a highly reverberant connection that is laterally affixed via point loading.

Alternatively, the backing section is cylindrical in shape and is disposed symmetrically relative to the extended axis of the elongated prosthesis body, wherein the cylinder protrudes from the elongated prosthesis body into the receiving space.

Alternatively, the backing section is plunger-shaped and is disposed symmetrically relative to the extended axis of the elongated prosthesis body, wherein a plunger shank carrying the plunger body protrudes from the elongated prosthesis body into the receiving space.

These embodiments can be developed in different ways depending on the specific conditions of the patient, in particular depending on the exact shape of the head of the stapes. In a variation, the plunger body has a concave contact surface directed into the receiving space, which engages directly even if the head of the stapes could have a convex shape. The plunger body may also have a flat contact surface, which is directed into the receiving space.

In an alternative development, the plunger body has a convex contact surface directed into the receiving space, which engages directly even if the head of the stapes would have a concave shape.

In order to achieve increased flexibility and variability of the prosthesis, the elongated prosthesis body preferably comprises at least one joint, in particular a ball joint, which has the advantage that the prosthesis can also compensate for hydrostatic forces.

Developments are advantageous in terms of particularly high postsurgical mobility of the prosthesis in which a plurality of adjoining, further rotary elements are provided, preferably in the form of a ball joint chain. The ball joint chain makes it easy to vary the length of the prosthesis by pushing the ball chain through the joint receptacle and subsequently remove the overhanging, uppermost balls.

The ball joint comprises a ball attached on the end of the prosthesis body thereof facing the second coupling element, a sleeve covering the ball on the side thereof remote from the second coupling element and a recess in the side facing the second coupling element, which functions as a socket for the ball. The ball joint is subjected to a soft support and therefore absorbs damping.

Also, the sleeve of the ball joint integrated into the prosthesis body is formed of a plastic sealing compound, preferably a silicone sealing compound.

The prosthesis is designed according to the particular defect to be eliminated or at least ameliorated in terms of its effect on the patient via use of the ossicular prosthesis according to the invention.

In an embodiment, the first attaching element comprises a top plate designed to rest on the tympanic membrane. Alternatively, the prosthesis is attached on one side, for example, to the limb of incus or to the manubrium of malleus. In this context, the ossicular prosthesis may be advantageously disposed at the end of the hammer (=umbo) or directly adjacent thereto, thereby resulting in the greatest leverage for the mechanical transmission of sound via motions that occur in the artificial or natural ossicular chain.

In addition to the postsurgical shifting of position, a further problem results once the ossicular prostheses have been implanted. That is, the middle ear of the human body may be described as a "semi-open region" whereby any implantation material that is inserted in the body within the scope of reconstruction of the middle ear and its structures thereby undergoes a particular stress that predominates in a contaminated and infected environment and which typically attacks the material. Since the objective of implanting an ossicular prosthesis must always be to enable the implant to remain in the patient's middle ear for as long as possible without complications occurring, a sustained attack on the material may result in damage being done to the prosthesis and/or in a local infection. Neither of these consequences is tolerable.

One embodiment is configured to permanently prevent damage from occurring to the implantation material or the surrounding tissue by coating the surface of the ossicular prosthesis entirely or at least in sections with a biologically active coating, in particular a growth-inhibiting and/or growth-promoting and/or antibacterial coating. A first attaching element, which is designed as a top plate of the ossicular prosthesis according to the invention should always have a growth-promoting coating.

The ossicular prosthesis or parts thereof may be made of titanium and/or gold and/or tantalum and/or steel and/or an alloy of said metals. It is known that titanium, in particular, in addition to being stiff and having excellent sound-conducting properties also exhibits excellent biocompatibility with the human ear.

In a particularly advantageous embodiment, the second coupling element is made, entirely or in part, of titanium or a material having a memory effect and/or superelastic properties such as Nitinol. Although the use of materials of this type is known per se in the field of ossicular prostheses, it proves particularly effective in conjunction with the present invention in particular.

In terms of the postsurgical position adjustment described above, it is advantageous for the entire prosthesis or parts thereof, for example, including the first coupling element, to be made of a material having memory effect or superelastic properties, preferably being made of Nitinol, as is known per se, for example, from WO 02/069850 A1 or U.S. Pat. No. 6,554,861 B2.

Alternatively, or in addition thereto, parts of the ossicular prosthesis may be composed of a ceramic material.

In an embodiment, the entire prosthesis or parts thereof are made of biocompatible plastics, particularly silicone, polytetrafluoroethylene (PTFE) or fibrous composite materials. With these materials, postsurgical rejection reactions may also be prevented in most cases.

BRIEF DESCRIPTION OF THE DRAWINGS

Further features and advantages of the invention will become apparent from the description of exemplary embodiments that follows, with reference to the attached figures, wherein:

FIG. 6b depicts an embodiment that is similar to the embodiment of FIG. 6a, although comprising a flat contact surface;

FIG. 8a shows a schematic cross-sectional view of an ossicular prosthesis in the region of the bell-shaped, second coupling element, which is seated on the head of the stapes and has a hemispherical backing section;

FIG. 8b depicts an embodiment that is similar to the embodiment of FIG. 8a, although comprising a second coupling element configured according to known second coupling elements.

DESCRIPTION OF THE PREFERRED EMBODIMENTS

The following is a detailed description of example embodiments of the Invention depicted in the accompanying drawings. The example embodiments are presented in such detail as to clearly communicate the invention and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present invention, as defined by the appended claims.

Figure 1A:
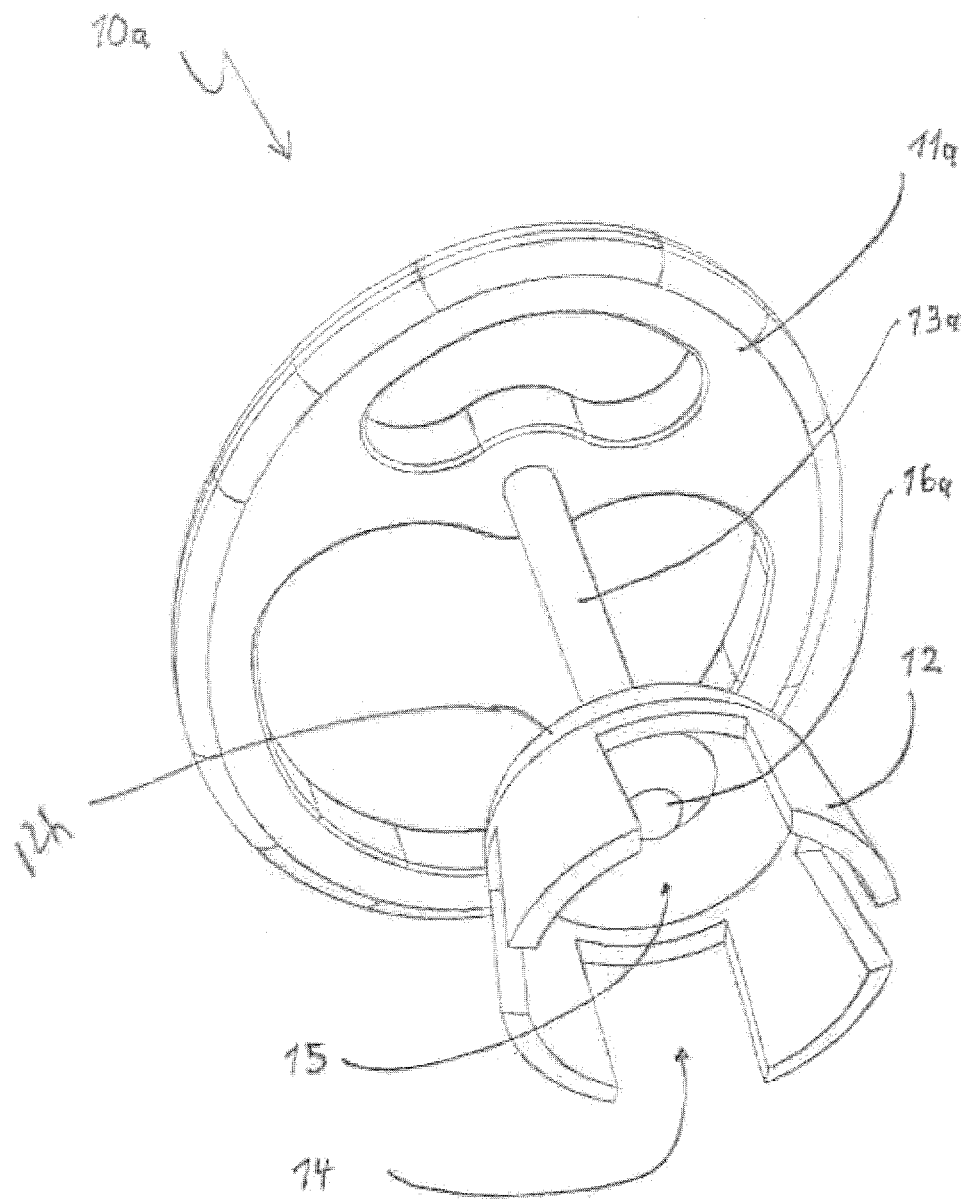
FIG. 1a is a schematic spatial depiction of a first embodiment of the ossicular prosthesis comprising a tympanic membrane top plate as the first attaching element, a bell-shaped second attaching element for placement against the head of the stapes and a backing section that extends into the receiving space of the second attaching element.

The embodiments of the ossicular prosthesis 10a; 10b; 10c; 20a; and 20b of the invention are depicted schematically in FIGS. 1a; 1b; 1c; 2a; and 2b, respectively, but which differ in terms of the detailed design thereof, each comprise, at one end, a first coupling element 11a; 11b; 11c; 21, which is used for the mechanical connection of the prostheses to a component of the ossicular chain and, is designed as the tympanic membrane top plate for placement against the tympanic membrane, or as a connecting piece 21 for the sound-conducting connection to an actuator end piece of an active hearing implant. Seated at the other end of the ossicular prostheses 10a; 10b; 10c; 20a; 20b is a second coupling element 12; 12'; 12"; 22; 82, respectively, which comprises an access opening 14; 24; 84 into a receiving space 15; 25; 85 and is designed as a bell or clip for a mechanical connection of the prosthesis to the stapes S, in particular to the head of the stapes C. Disposed therebetween is an elongated prosthesis body 13; 13a; 13b; 13c; 13d; 23 in the form of an elongated shank, which connects the two attaching elements 11; 21; 31; 41; 51 and 12; 22; 32; 42; 52 to one another in a sound-conducting manner.

The second coupling elements 12; 12'; 12"; 22 are geometrically designed in each case such that to comprise a backing section 16a; 16b; 16c; 16d; 16e; 16f; 16g; 16h; 16i; 26 on the inner surface of the receiving space 15; 25, as an axial extension of the elongated prosthesis body 13; 13a; 13b; 13c; 13d; 23. The backing sections project from the elongated prosthesis body 13; 13a; 13b; 13c; 13d; 23 into the receiving space 15; 25 and, in the implanted state of the ossicular prosthesis 10a; 10b; 10c; 20a; 20b, bear against the stapes S. In particular, the backing sections 16a; 16b; 16c; 16d; 16e; 16f; 16g; 16h; 16i; 26 bear against the head of the stapes C and prevent or minimize the formation of a hollow space between the stapes S and the inner surface of the receiving space 15; 25 in the axial extension of the elongated prosthesis body 13; 13a; 13b; 13c; 13d; 23.

Figure 1B:
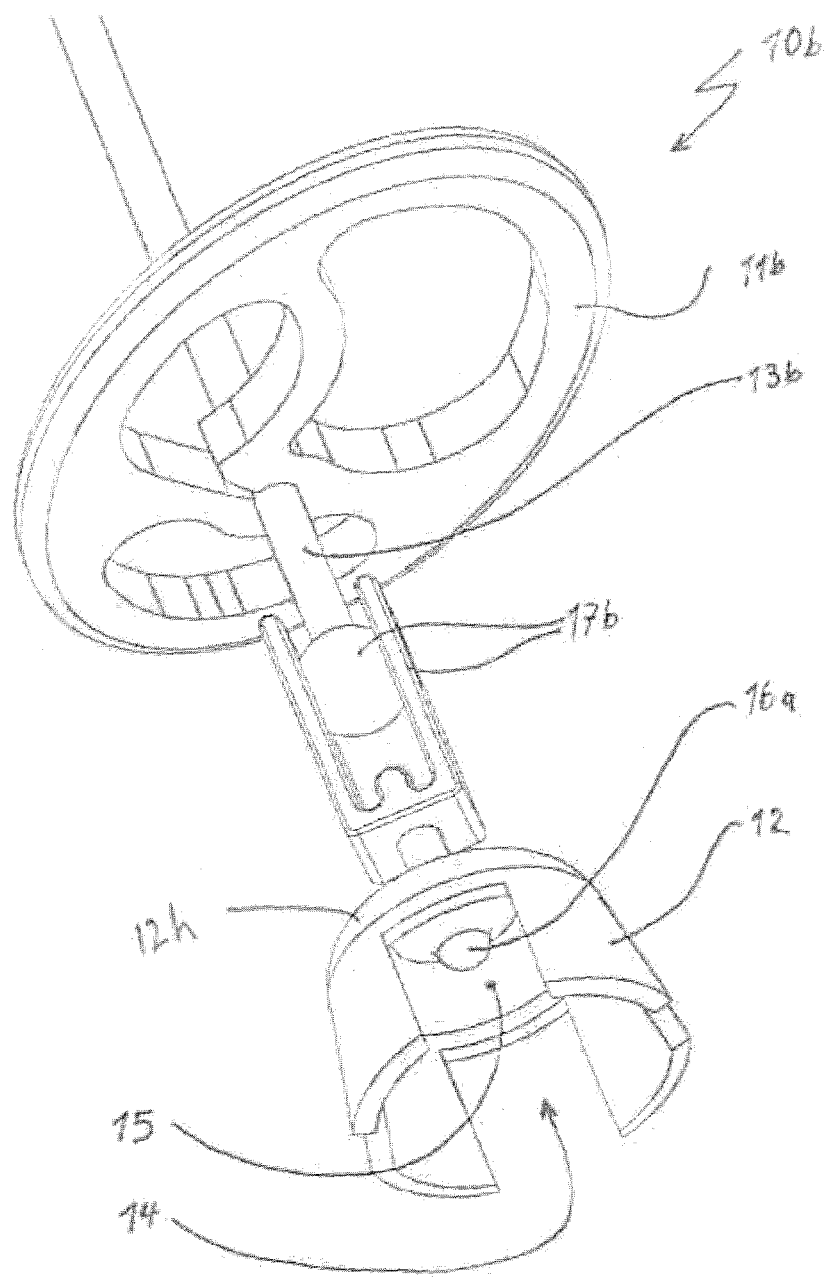
FIG. 1b depicts an embodiment comprising a ball joint in the prosthesis body.
Figure 1C:
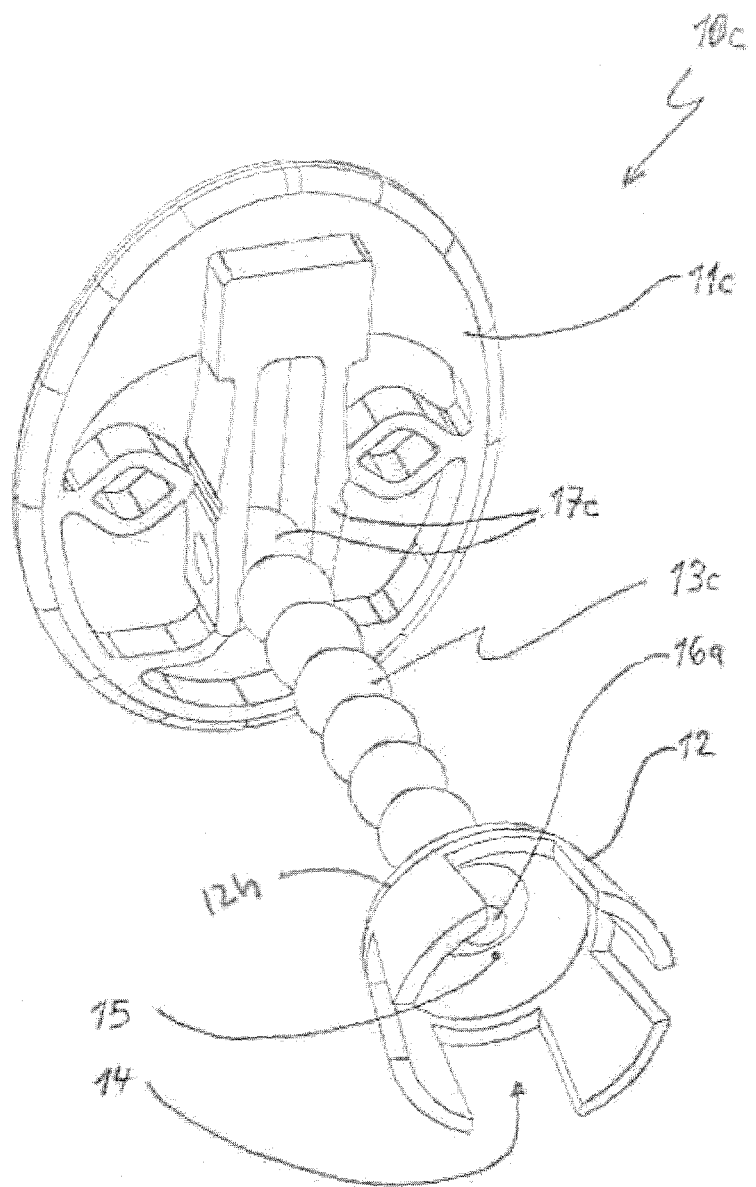
FIG. 1c depicts a variable-length embodiment comprising a ball chain.

In the embodiments shown in FIGS. 1a, 1b and 1c, the first attaching element 11a; 11b; 11c is designed as a top plate for placement against the tympanic membrane. In FIGS. 1a, 1b, 1c, 2a and 3a-8a, the second coupling element 12 at the end of the elongated prosthesis body 13; 13a; 13b; 13c; 13d; 23 opposite the top plate is designed as a bell having several slots for placement against the head of the stapes, and is fastened via the bell hood at one end of the elongated prosthesis body 13; 13a; 13b; 13c; 13d; 23. The bell-shaped coupling elements 12 in FIGS. 1a-2a each comprise a roundly arched bell hood 12h, and the bell-shaped coupling element 12' in FIGS. 3a-8a each comprise a flattened bell hood 12h', and in FIG. 7 comprise a bell hood 12h" that is indented at the top.

Figure 2A:
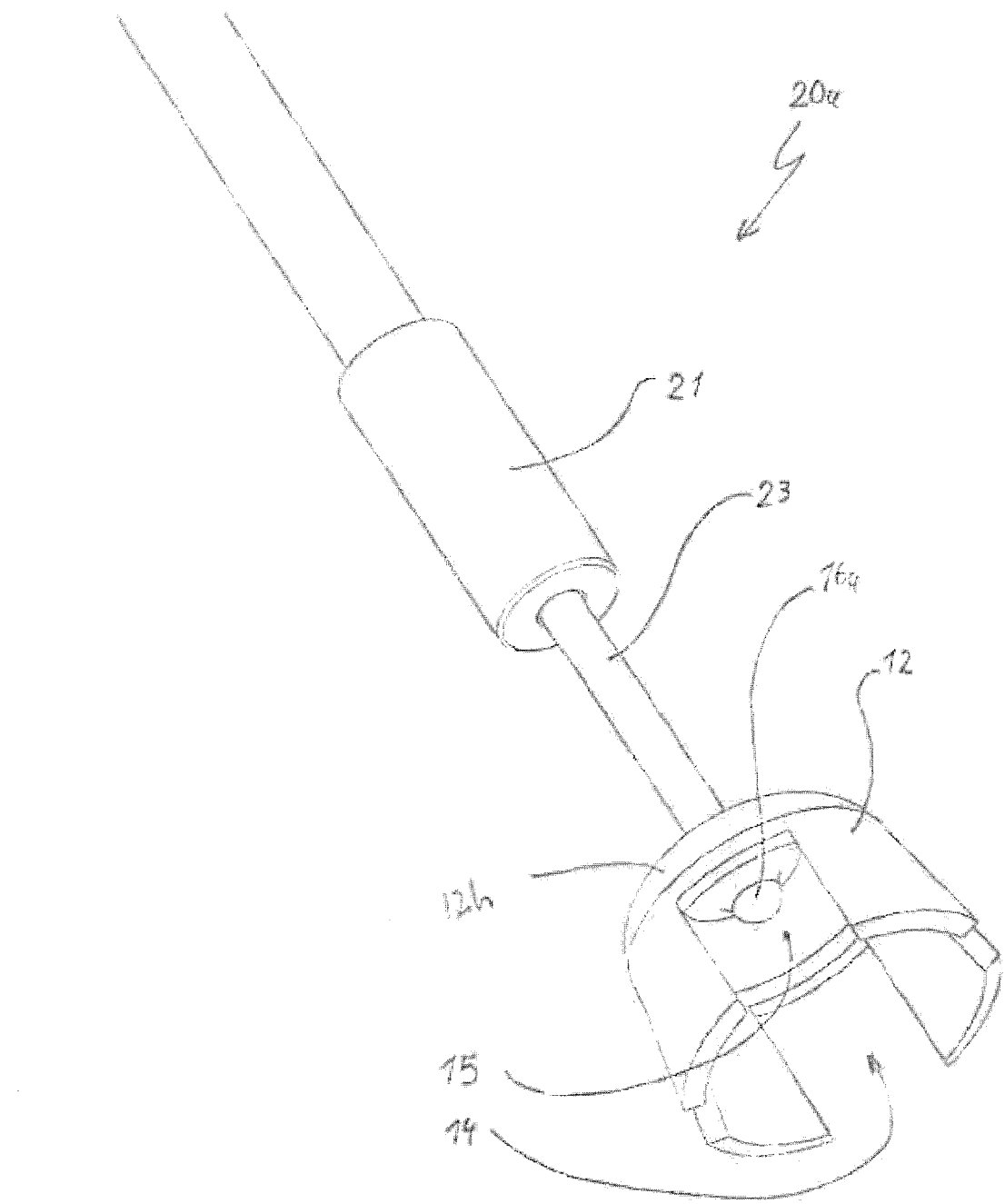
FIG. 2a depicts an embodiment comprising a first attaching element designed as a connecting piece for the sound-conducting connection to an actuator end piece of an active hearing implant and a bell having a plurality of slots as the second attaching element.
Figure 2B:
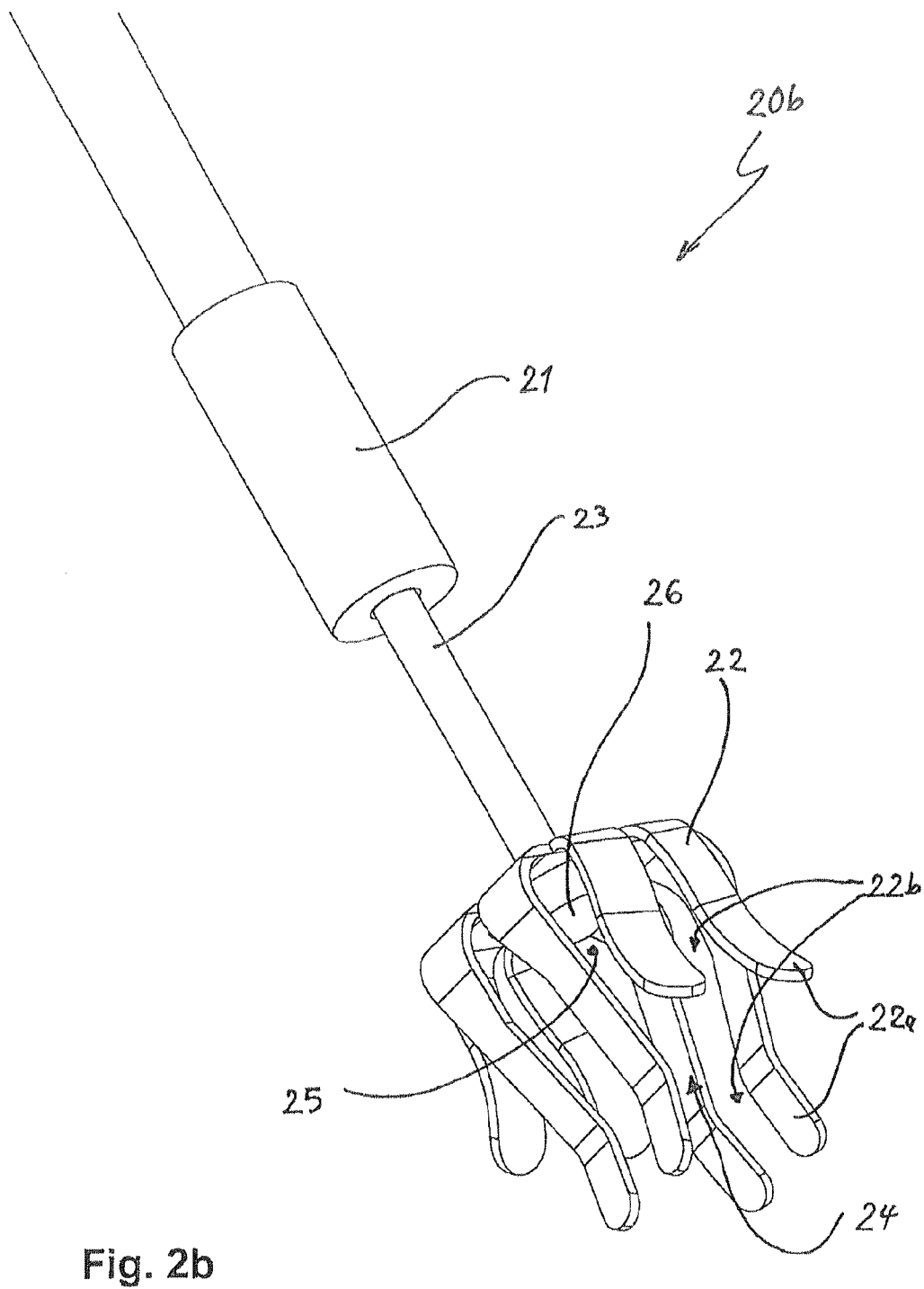
FIG. 2b depicts the embodiment as in FIG. 2a comprising a clip-shaped, second attaching element having a plurality of respectively alternating, lateral blades and slots.
Figure 3A:
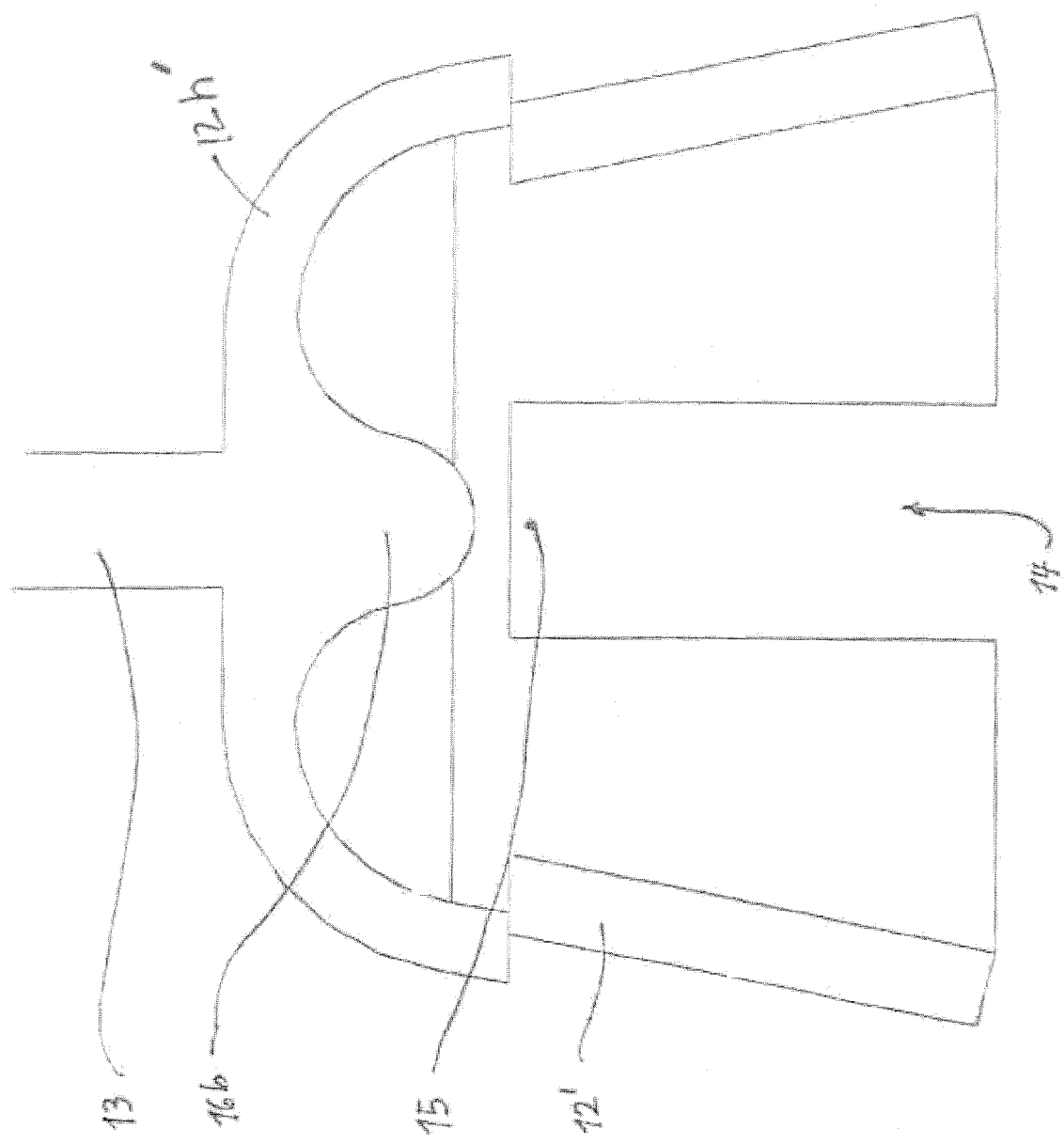
FIG. 3a presents a schematic cross-sectional view in the region of a second attaching element designed as a slotted bell and comprising a hemispherical backing section.
Figure 3B:
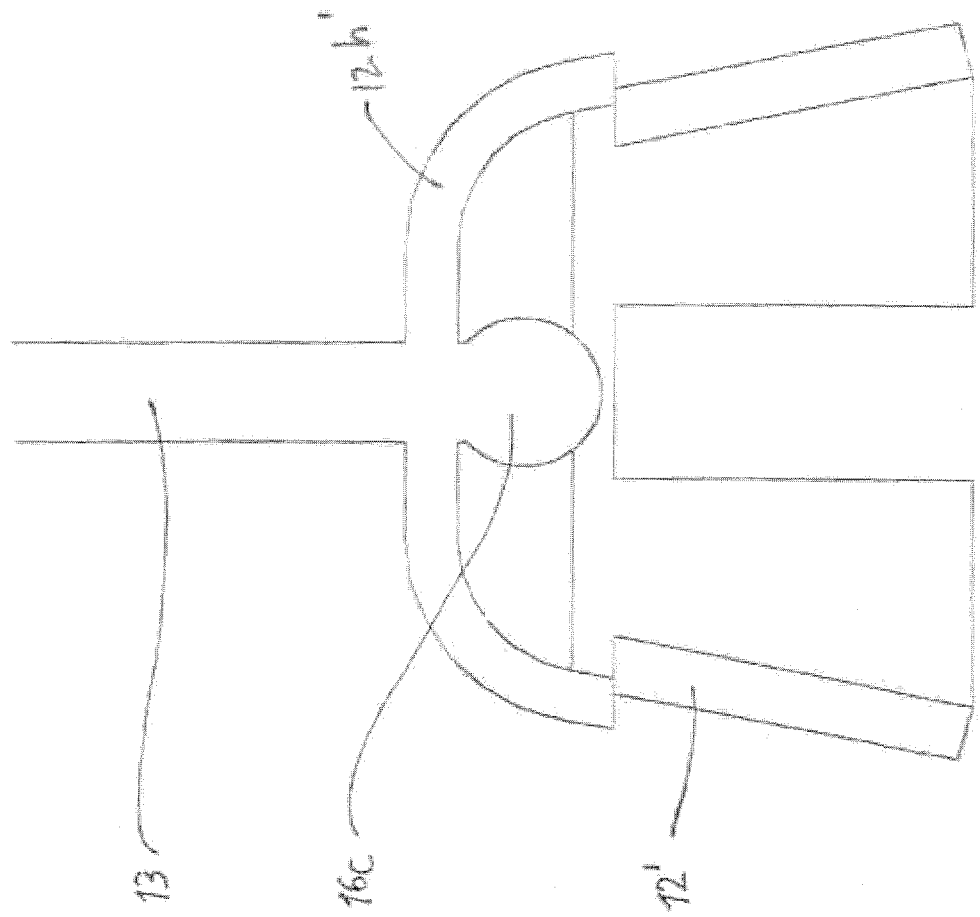
FIG. 3b depicts an embodiment similar to the embodiment of FIG. 3a, wherein the backing section is spherical.

In the embodiments shown in FIGS. 2a and 2b, the first coupling element 21 is designed as a connecting piece for the sound-conducting connection to an actuator end piece of a non-illustrated, active hearing implant. The second coupling element 22 in FIG. 2b is designed as a clip, which comprises a plurality of respectively alternating, lateral blades 22a and slots 22b. The backing section 16a; 16b; 16c; 16i; 26 in the embodiments of FIGS. 1a-3b, 7 and 8a is spherical or ellipsoid and is disposed symmetrically relative to the extended axis of the elongated prosthesis body 13; 13a; 13b; 13c; 13d; 23.

Figure 4:
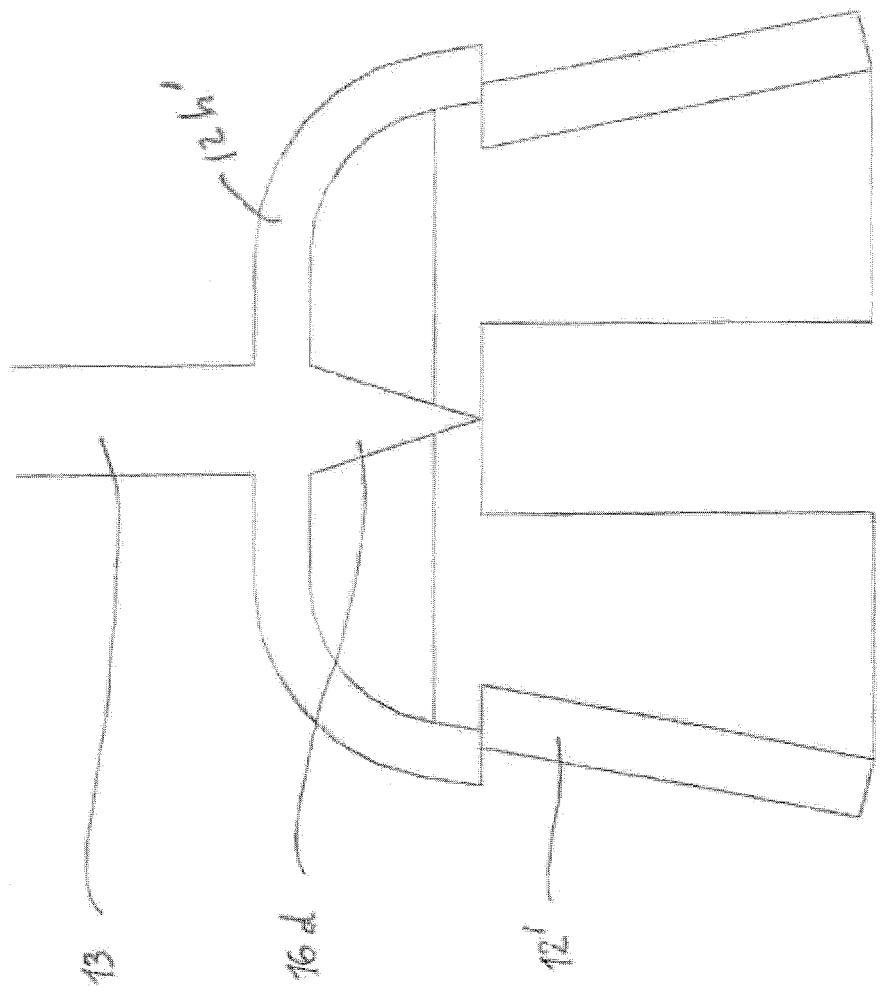
FIG. 4 depicts an embodiment similar to the embodiment of FIG. 3a, wherein the backing section is conical.
Figure 5:
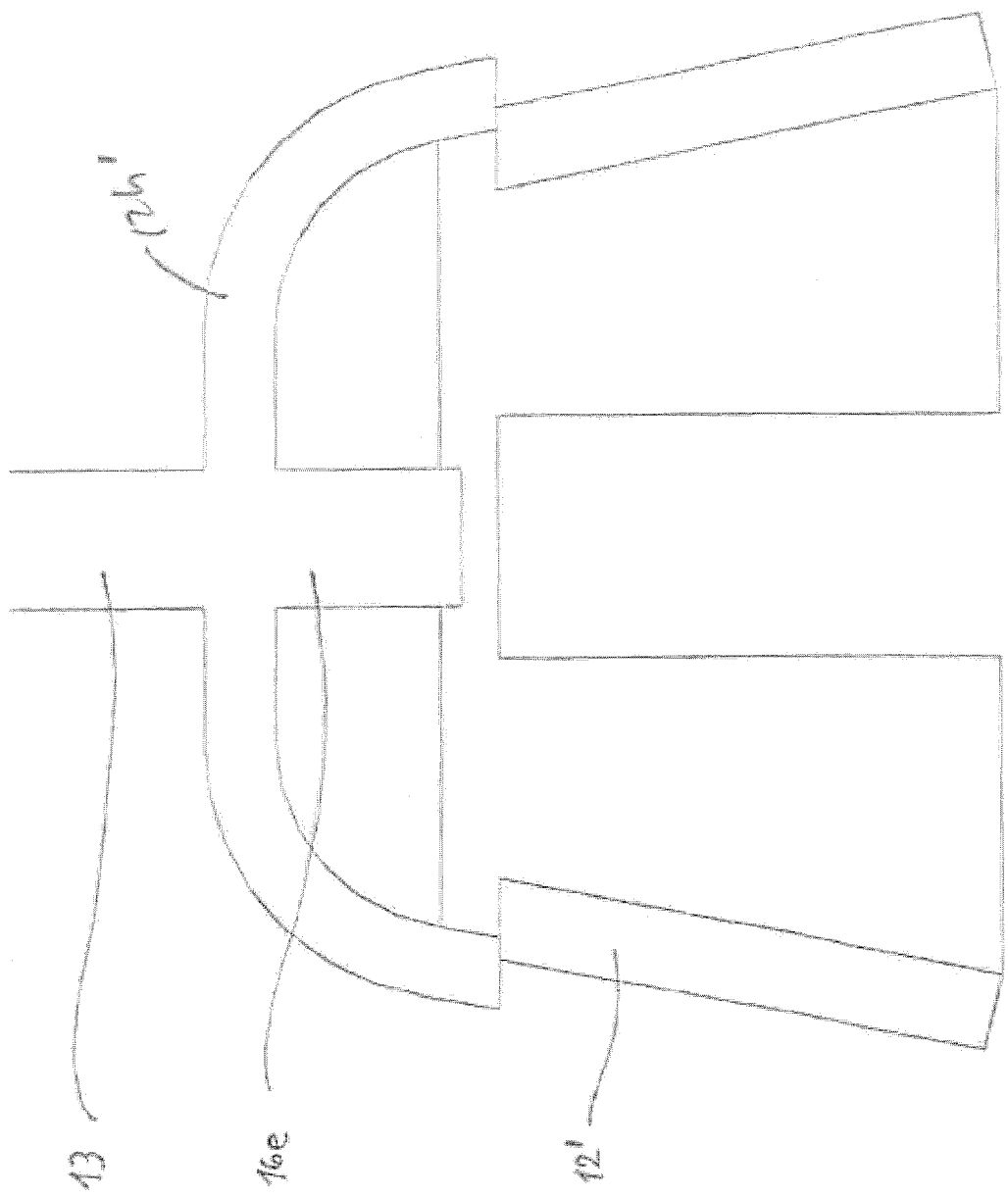
FIG. 5 depicts an embodiment similar to the embodiment of FIG. 3a, wherein the backing section is cylindrical.

In the embodiment of FIG. 4, the backing section 16d is conical, while the bell-shaped coupling element 12' in FIG. 5 has a cylindrical backing section 16e.

Figure 6A:
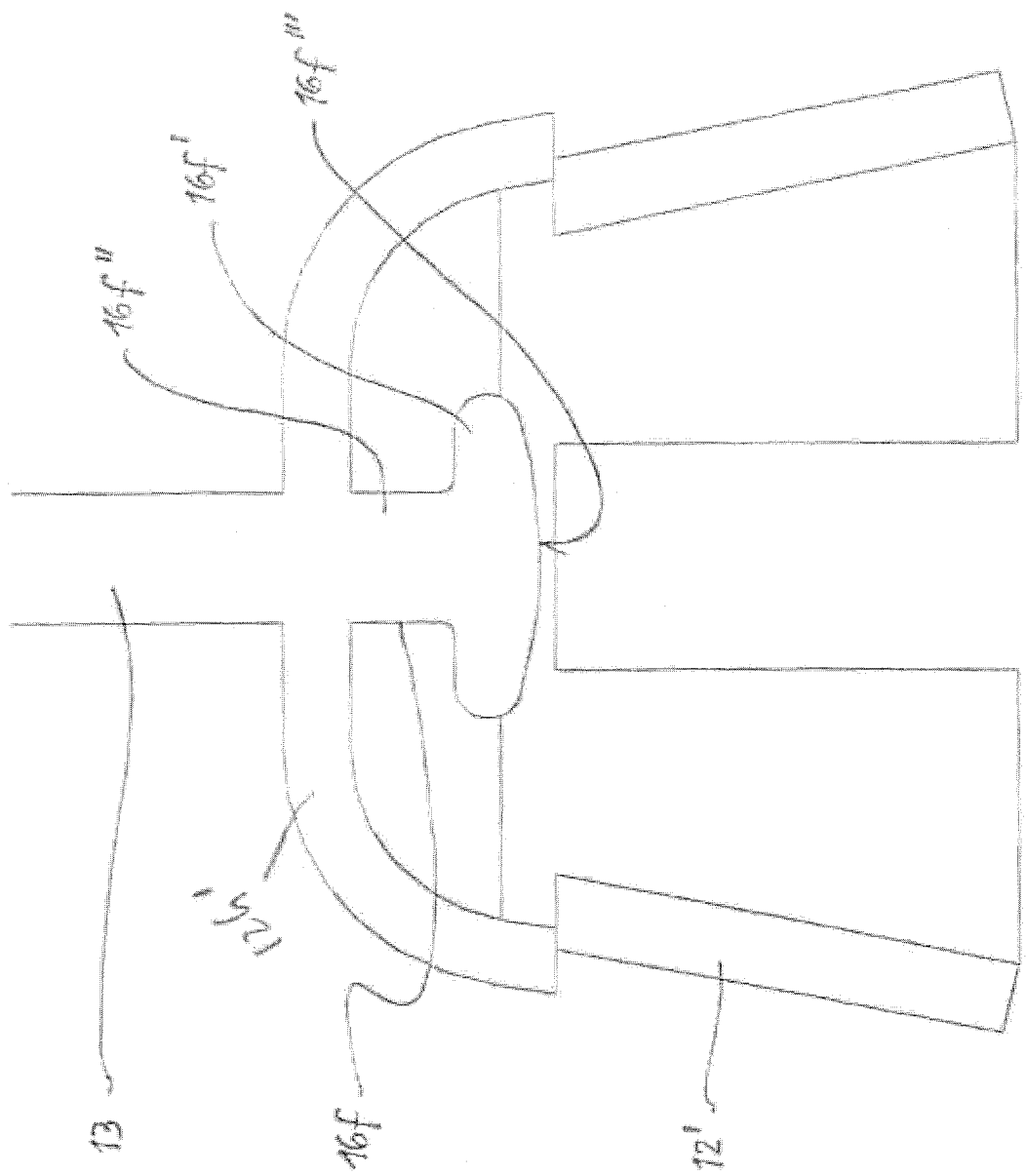
FIG. 6a depicts an embodiment similar to the embodiment of FIG. 3a, wherein the backing section is plunger-shaped and a concave contact surface is directed into the receiving space of the bell.
Figure 6C:
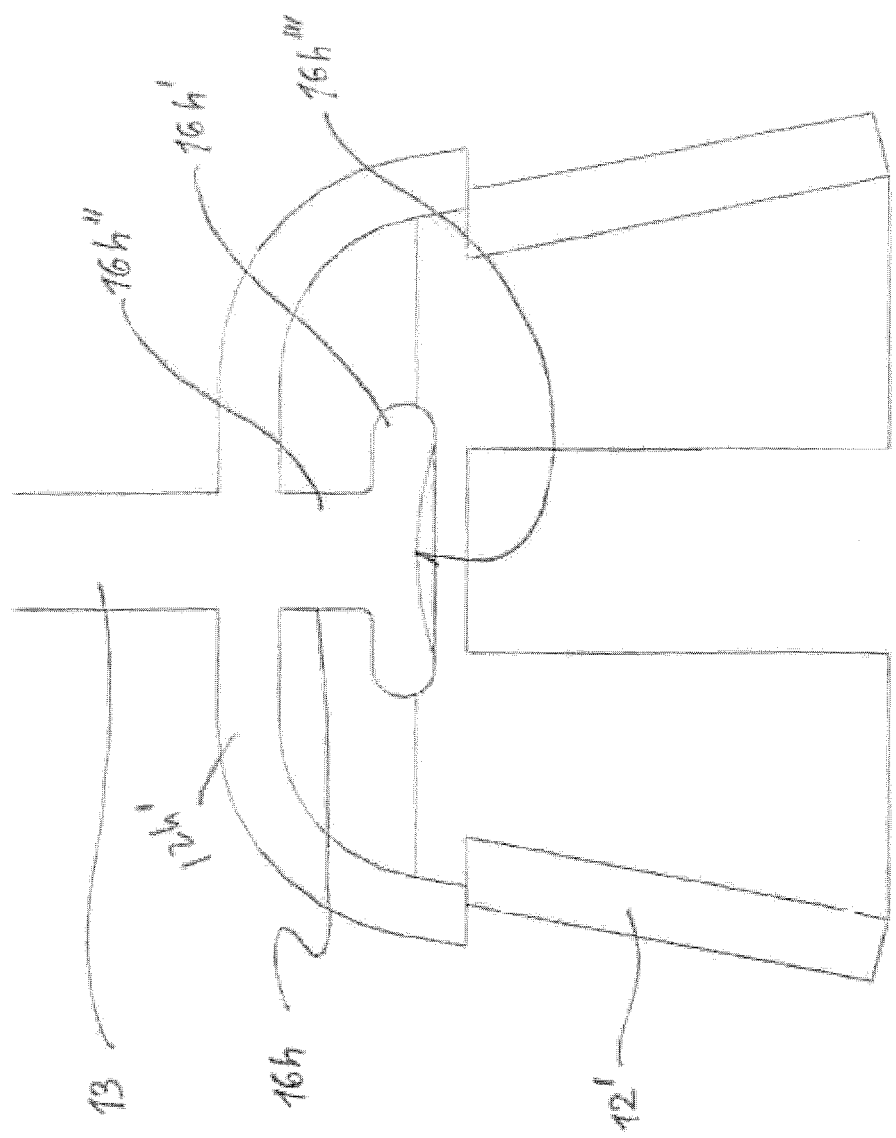
FIG. 6c depicts an embodiment that is similar to the embodiment of FIG. 6a, although comprising a convex contact surface.
Figure 7:
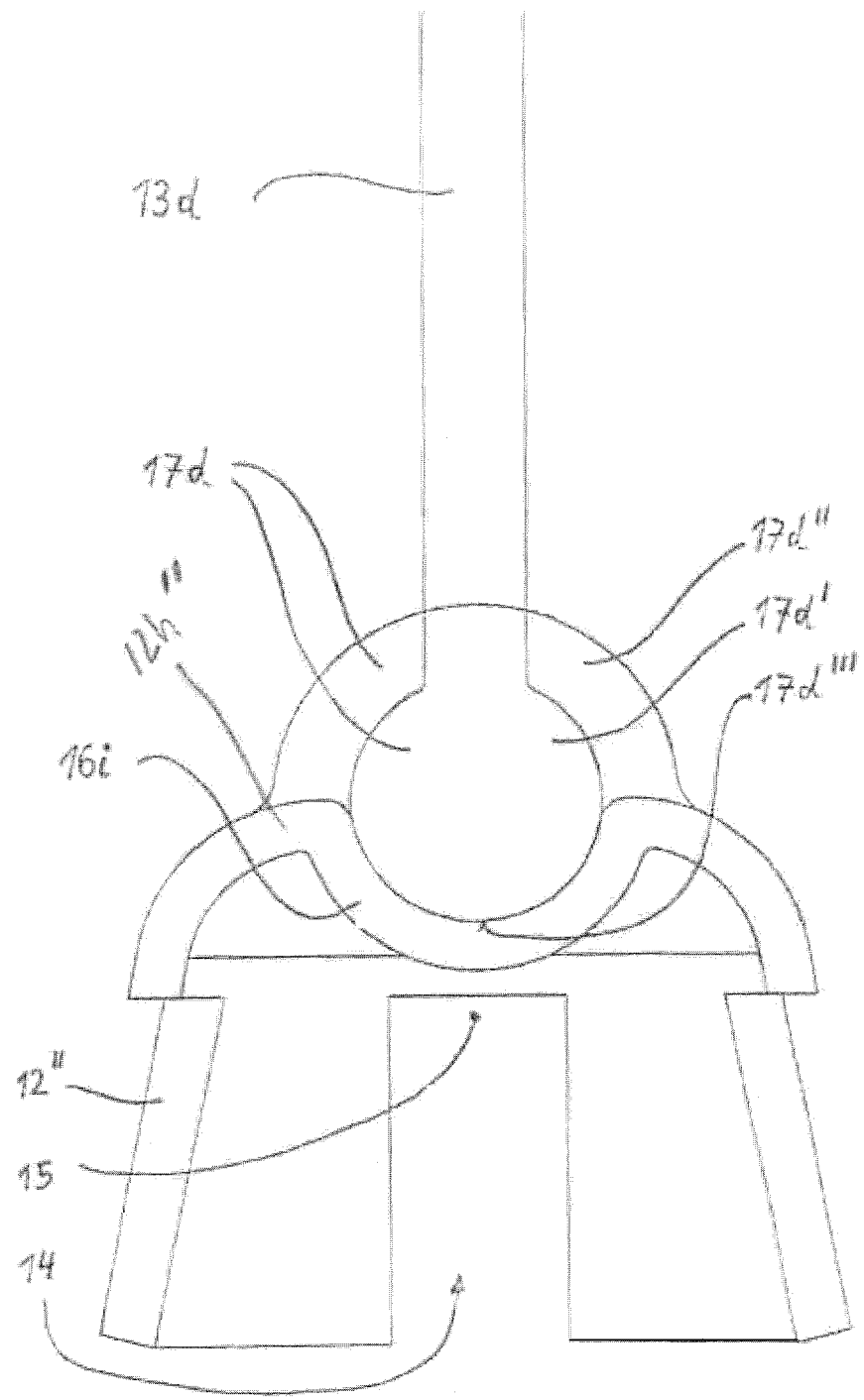
FIG. 7 depicts an embodiment that is similar to the embodiment of FIG. 6a, although comprising a ball joint integrated into the end of the prosthesis body and configured so that the backing section of the second attaching element is designed as a socket.

In FIGS. 6a-6c, the backing sections 16f; 16g; 16h are each shaped as plungers and are disposed symmetrically relative to the extended axis of the elongated prosthesis body 13, wherein a plunger shank 16f"; 16g"; 16h" carrying the plunger body 16f; 16g'; 16h' protrudes from the elongated prosthesis body 13 into the particular receiving space 15. In the embodiment according to FIG. 6a, the plunger body 16f' has a concave contact surface 16f"', which is directed into the receiving space 15; in FIG. 6b has a flat contact surface 16g"'; and in FIG. 6c has a convex contact surface 16h"'. In the embodiments of FIGS. 1b, 1c and 7, the elongated prosthesis body 13b; 13c; 13d comprises at least one joint, in particular a ball joint 17b; 17c; 17d.

While the ball joint 17b of the ossicular prosthesis 10b in FIG. 1b is integrated into a shank-shaped, elongated prosthesis body 13b, the ossicular prosthesis 10c in FIG. 1c comprises an elongated prosthesis body 13c designed as a ball chain. This ball chain can be guided through a receiving section in the first coupling element 11c, which is designed as a tympanic membrane top plate, and can be cut to the length required in the particular case. The remaining uppermost ball of the elongated prosthesis body 13 then forms a ball joint 17c together with the receiving section.

In the embodiment of FIG. 7, the ball joint 17d comprises a ball 17d', which is mounted on the end of the prosthesis body 13d thereof facing the second coupling element 1", a sleeve 17d", which covers the ball 17d' on the side thereof remote from the second coupling element 12", and a recess 17d"'. Recess 17d"' is indented in the outer surface of the bell hood 12h" of the second coupling element 12" and functions as a socket for the ball 17d'. The sleeve 17d" is formed of a plastic sealing compound, preferably of a silicone sealing compound. The inner side of the bell hood 12h" facing the receiving space 15 forms a hemispherical backing section 16i due to the above-described indentation.

In FIG. 8a, a prosthesis that has been modified with a backing section 16b in the bell-shaped, second coupling element 12' thereof is shown for the purpose of visual comparison with an ossicular prosthesis according to the prior art, which is shown in FIG. 8b. It is clear that, in the conventional prosthesis in FIG. 8b, a hollow space necessarily remains exposed specifically between the axial extension of the elongated prosthesis body 83 and the head of the stapes C, which has an extremely negative effect on the sound conduction in the direction of the inner ear. By contrast, it is precisely this hollow space in the extension of the elongated prosthesis body 13 in the prosthesis according to the invention, which is shown in FIG. 8a, which is reliably prevented by means of the backing section 16b.

Figure 9C:
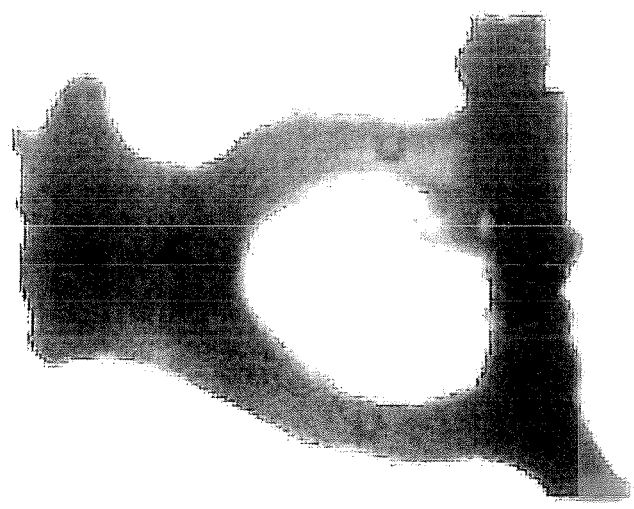
FIGS. 9a-c provide three photographic views, each at the same magnification, but each depicting different, partially pathologically altered, human heads of stapes of different geometries, respectively.
Figure 9B:
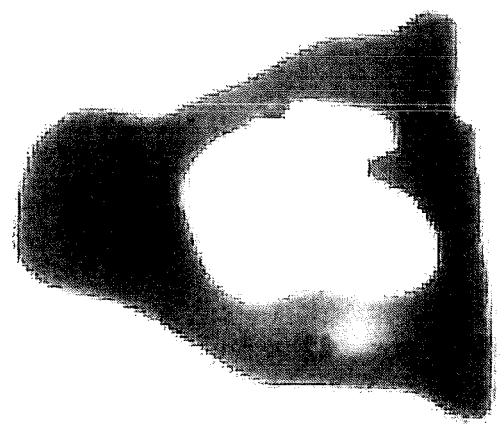
Figure 9A:
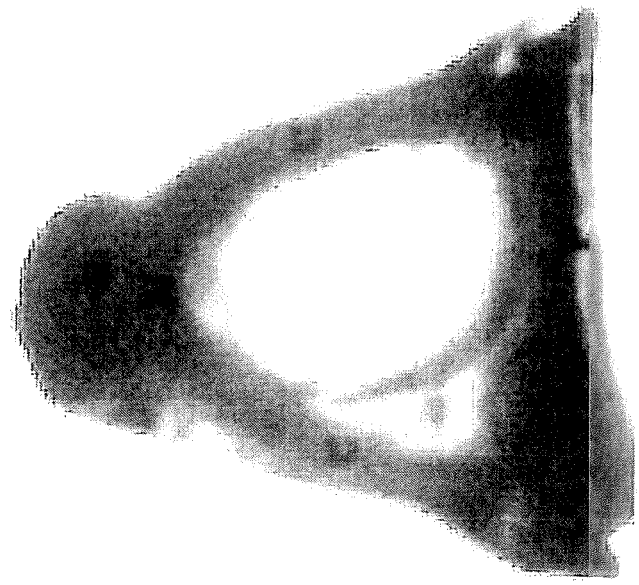

Finally, FIG. 9a, 9b, 9c are three photographs of human stapes bones, respectively, each having the same magnification. Clearly shown are considerable differences in the geometric shape of the stapes, in particular in the region of the head of the stapes, and the markedly different sizes of the particular stapes bone. The respective photographs highlight the details of the different stapes bones, which are partially caused by pathological processes or are due simply to the natural, individual deviation between one patient and another. Clearly demonstrated are the decisive advantages offered by the possible variations of an ossicular prosthesis modified according to the invention as compared to a conventional prosthesis according to the prior art in terms of solving a problem in an individualized manner. Due to the various possible designs of the backing section provided according to the invention, optical sound conduction can be ensured specifically in the region of the head of the stapes.

As will be evident to persons skilled in the art, the foregoing detailed description and figures are presented as examples of the invention, and that variations are contemplated that do not depart from the fair scope of the teachings and descriptions set forth in this disclosure. The foregoing is not intended to limit what has been invented, except to the extent that the following claims so limit that.

What is claimed is:

1. An ossicular prosthesis designed to replace or bridge at least one element of a human ossicular chain, comprising:
a sound-conducting, elongated prosthesis body;
on a first end of the elongated prosthesis body, a first coupling element designed as a top plate configured for placement of the prosthesis against a tympanic membrane, or as a clip for mechanical connection to a component of the ossicular chain or as a connecting piece for a sound-conducting connection to an actuator end piece of an active hearing implant on a first end; and on a second end of the elongated prosthesis body, a second coupling element having an access opening in a receiving space is designed as a bell or clip configured to receive a stapes or a head of the stapes and mechanically connect the prosthesis thereto; wherein the second coupling element comprises a backing section that projects from an inner surface of the receiving space, as an axial extension of the elongated prosthesis body so that the backing section is configured to bear against the stapes or the head of the stapes in the receiving space and prevents or minimizes the formation of a hollow space between the stapes and the inner surface of the receiving space in the axial extension of the elongated prosthesis body.

2. The ossicular prosthesis according to claim 1, wherein the second coupling element is designed as a bell having several slots on a side and is fastened via a bell hood at one end of the elongated prosthesis body.

3. The ossicular prosthesis according to claim 2, wherein the bell has a roundly arched bell hood.

4. The ossicular prosthesis according to claim 2, wherein the bell has a bell hood that is flattened, is indented from above or both.

5. The ossicular prosthesis according to claim 1, wherein the second coupling element is designed as a clip having a plurality of respectively alternating, lateral blades and slots.

6. The ossicular prosthesis according to claim 1, wherein the backing section is spherical or ellipsoid and is disposed symmetrically relative to the extended axis of the elongated prosthesis body.

7. The ossicular prosthesis according to claim 1, wherein the backing section is conical in shape and is disposed symmetrically relative to the extended axis of the elongated prosthesis body and wherein a cone tip protrudes from the elongated prosthesis body into the receiving space.

8. The ossicular prosthesis according to claim 1, wherein the backing section is cylindrical in shape and is disposed symmetrically relative to the extended axis of the elongated prosthesis body and wherein a cylinder protrudes from the elongated prosthesis body into the receiving space.

9. The ossicular prosthesis according to claim 1, wherein the backing section is shaped as a plunger and is disposed symmetrically relative to the extended axis of the elongated prosthesis body, and wherein a plunger shank carrying a plunger body protrudes from the elongated prosthesis body into the receiving space.

10. The ossicular prosthesis according to claim 9, wherein the plunger body comprises a concave contact surface directed into the receiving space.

11. The ossicular prosthesis according to claim 9, wherein the plunger body comprises a flat contact surface directed into the receiving space.

12. The ossicular prosthesis according to claim 9, wherein the plunger body comprises a convex contact surface directed into the receiving space.

13. The ossicular prosthesis according to claim 1, wherein the elongated prosthesis body comprises at least one joint.

14. The ossicular prosthesis according to claim 13, wherein the joint comprises a ball mounted on an end of the elongated prosthesis body thereof facing the second coupling element, a sleeve that covers the ball on the side thereof remote from the second coupling element and a recess in a side facing the second coupling element that functions as a socket for the ball.

15. The ossicular prosthesis according to claim 14, wherein the sleeve is formed of a plastic sealing compound.

* * * * *